United States Patent
Peng et al.

(10) Patent No.: US 12,365,699 B2
(45) Date of Patent: Jul. 22, 2025

(54) ELASTASE INHIBITOR PRODRUG AND USE THEREOF

(71) Applicant: SUZHOU ARK BIOPHARMACEUTICAL CO., LTD., Suzhou (CN)

(72) Inventors: Cheng Peng, Suzhou (CN); Yang Zhou, Suzhou (CN); Yanfei Wang, Suzhou (CN); Mengfei Qian, Suzhou (CN); Zhaoxiong Cai, Suzhou (CN); Gang Zou, Suzhou (CN); Haiqing Yuan, Suzhou (CN); Zhen Jim Wu, Suzhou (CN)

(73) Assignee: SUZHOU ARK BIOPHARMACEUTICAL CO., LTD., Suzhou (CN)

( * ) Notice: Subject to any disclaimer, the term of this patent is extended or adjusted under 35 U.S.C. 154(b) by 587 days.

(21) Appl. No.: 17/908,296

(22) PCT Filed: Mar. 8, 2021

(86) PCT No.: PCT/CN2021/079500
§ 371 (c)(1),
(2) Date: Aug. 31, 2022

(87) PCT Pub. No.: WO2021/180023
PCT Pub. Date: Sep. 16, 2021

(65) Prior Publication Data
US 2023/0107378 A1  Apr. 6, 2023

(30) Foreign Application Priority Data
Mar. 9, 2020  (CN) .......................... 202010155890.9

(51) Int. Cl.
C07F 5/02 (2006.01)
(52) U.S. Cl.
CPC .................... C07F 5/027 (2013.01)
(58) Field of Classification Search
CPC ........................................ C07F 5/027
See application file for complete search history.

(56) References Cited

U.S. PATENT DOCUMENTS

| 5,948,886 A | 9/1999 | Peet et al. |
| 6,172,044 B1 | 1/2001 | Peet et al. |
| 6,339,107 B1 | 1/2002 | Belloni |

FOREIGN PATENT DOCUMENTS

| CN | 87107753 A | | 6/1988 | |
| CN | 1173179 A | | 2/1998 | |
| CN | 1649831 A | | 8/2005 | |
| CN | 110799193 | * | 2/2020 | ............. A61K 31/69 |
| CN | 110799193 A | | 2/2020 | |

* cited by examiner

*Primary Examiner* — Erich A Leeser
(74) *Attorney, Agent, or Firm* — SZDC Law PC

(57) ABSTRACT

The present disclosure provides an elastase inhibitor prodrug and use thereof, being a compound of formula I or a pharmaceutically acceptable salt, ester, isomer or solvate thereof, prodrugs or isotopically labeled compound. Compared with the compound 52 (control example) in WO 2018/175173 A1, the compound disclosed herein has the advantages of high pulmonary exposure and long half-life. The prodrugs of the present disclosure significantly increase the concentration and residence time of the active compound (control example) in the lungs with significant improvements in pharmacokinetics in vivo compared to the control example.

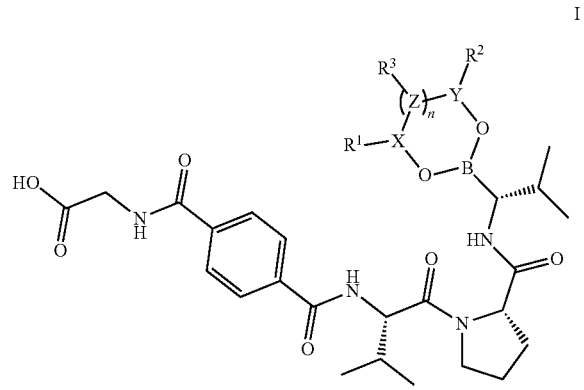

20 Claims, 2 Drawing Sheets

ELASTASE INHIBITOR PRODRUG AND USE THEREOF

CROSS-REFERENCE TO RELATED APPLICATION(S)

The present disclosure is the National Stage Application of PCT/CN2021/079500, filed on Mar. 8, 2021, which claims the priority to the Chinese invention patent application No. 202010155890.9, entitled "elastase inhibitor prodrug and use thereof" which was filed on Mar. 9, 2020, and the content of which is incorporated herein by reference in its entirety.

TECHNICAL FIELD

The present disclosure belongs to the field of compound, specifically relates to a prodrug of substituted boronic acid compound and a mixture or composition comprising the prodrug of substituted boronic acid compound, especially the mixture or composition comprising the prodrug of substituted boronic acid compound as an elastase inhibitor for the treatment of various pulmonary diseases caused by excess elastase, including chronic obstructive pulmonary disease (COPD).

TECHNICAL BACKGROUND

Human neutrophil elastase (HNE) is a 32 kD serine protease which is involved in the pathological process of many diseases. Excess expression of elastase is destructive to the human body and the liver will specifically synthesize and secrete a natural inhibitor (alpha-1 antitrypsin) to maintain the balance of elastase activity in the human body. Elastase is stored in azurophilic granules after synthesized in neutrophils and is not secreted until neutrophils are activated by external signals (Takahashi H., Nukiwa T., Basset P., Crystal R. G., *J. Biol. Chem.*, 1988, 263(5): 2543-2547). Its main role is to degrade the elastin. Elastin is one of the main constituents of extracellular matrix proteins, and other constituents include fibronectin, laminin, proteoglycan, type III and type IV collagen (Bieth J. G., Elastases: catalytic and biological properties, in "Regulation of Matrix Accumulation", Mecham, R. P. (Eds), Academic Press, NY, USA, 1986, 217-306). The role of elastase includes fighting bacterial invasion by degrading bacterial structural proteins. In summary, human elastase can degrade damaged tissues or invading bacteria and play an indispensable role in maintaining body homeostasis.

Alpha-1 antitrypsin deficiency (A1AD) is a hereditary disorder characterized by the low level of alpha-1 antitrypsin as a natural inhibitor of elastase, in which an excess of the protease with balance loss begins to destroy extracellular matrix of bronchiolar and alveolar epithelial cells. (Laurell and Eriksson, Scand. *J. Clin. Lab. Invest.*, 1963, 15: 132-140). Its pathological process strongly supports the causal relationship between excess elastase activity and chronic lung injury diseases, especially conditions such as airflow limitation and emphysema. In another hereditary disorder cystic fibrosis, inactivated CFTR protein leads to excessively thick mucus in the trachea and chronic inflammation, and further yields excess accumulation of elastase, which ultimately damages the structure of lung tissue and limits its function.

In addition to the above two hereditary diseases, elastase also plays a critical role in several other chronic lung diseases, including pulmonary fibrosis, pneumonia, acute respiratory distress syndrome, chronic bronchiolitis, emphysema, etc. Chronic obstructive pulmonary disease (COPD) is a chronic lung disease caused by airflow limitation due to chronic airway inflammation and difficulty breathing owing to emphysema.

COPD is a high-morbidity disease. There are currently about 100 million COPD patients in China, and the number is increasing due to factors such as an aging population and air pollution. There is currently no effective treatment for the disease. Currently used bronchodilators (LABA/LAMA) can only relieve symptoms but cannot prevent the disease progression. These patients will continue to suffer from lung infections frequently, and the level of lung damage increases with each inflammation.

In conclusion, elastase inhibitors may have curative effect on the above diseases. Currently, several inhibitors have entered clinical trials, or are in clinical trials, which test the effect of treatment on diseases such as chronic obstructive pulmonary disease, cystic fibrosis, or alpha-1 antitrypsin deficiency. But these trials either failed or remained inconclusive. Most of the failures are not due to poor activity, but because of toxicity (covalent binding to elastase), pharmacokinetics (no lung enrichment), etc. WO 2018/175173 A1 mentions a boron-containing compound 52, the structure of which is shown below.

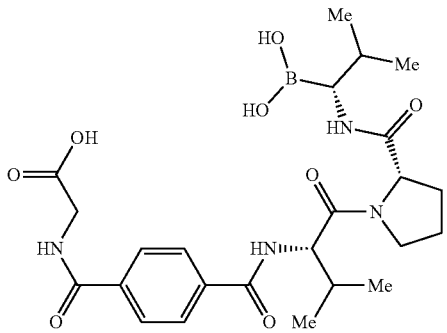 [SMILES: CC(C)[C@H](NC(=O)[C@@H]1CCCN1C(=O)[C@@H](NC(=O)c1ccc(C(=O)NCC(=O)O)cc1)C(C)C)B(O)O]

The compound is synthesized using innovative chemical methods and can reversibly covalently bound to elastase. It is a novel elastase inhibitor with excellent characteristics of high lung enrichment rate. However, research of pharmacokinetic studies of animals in vivo found that the compound has too short pulmonary exposure and rapid elimination, which may limit its efficacy. Therefore, there is an urgent need to develop a class of elastase inhibitors with longer and higher exposure in vivo.

SUMMARY OF THE DISCLOSURE

Problems to be Solved

To solve the above technical problems, the present disclosure provides a series of prodrugs with higher pulmonary exposure and longer half-life than Compound 52 in WO 2018/175173 A1.

Solutions

To solve the above technical problems, the present disclosure provides the following solutions:

A compound of formula I or a pharmaceutically acceptable salt, ester, isomer, solvate, prodrug or isotopically labeled compound thereof,

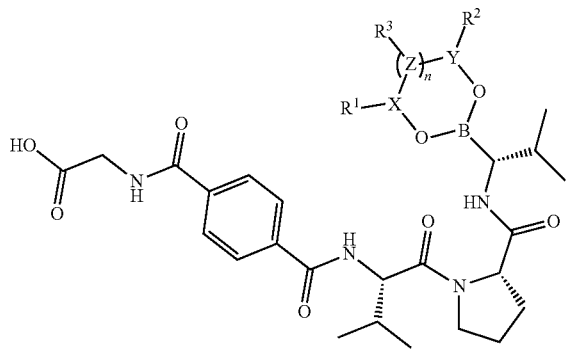

wherein,

When n is 0,

X and Y are directly connected, X and Y are $CR^4$ and $CR^5$ respectively;

$R^4$ and $R^5$ are each independently selected from hydrogen, deuterium and $C_{1-6}$ alkyl;

$R^1$ and $R^2$ are each independently selected from hydrogen, deuterium, halogen, $C_{1-6}$ alkyl and $C_{3-8}$ cycloalkyl, or $R^1$ and $R^2$ are connected to form a $C_{3-8}$ cycloalkane which is unsubstituted or substituted with one or more $R^6$;

If present, each of $R^6$ is independently selected from hydrogen, deuterium, hydroxy, amino, halogen, $C_{1-6}$ alkyl, halogen-substituted $C_{1-6}$ alkyl and $C_{1-6}$ alkoxy;

Or, when n is an integer from 1 to 5,

X—$R^1$ and Y—$R^2$ are each independently selected from carbonyl and $CHR^7$;

If present, each of $R^7$ is independently selected from hydrogen, deuterium and $C_{1-6}$ alkyl;

Each of Z is independently selected from O, S, CH and N, and when Z is O or S, $R^3$ is absent.

If present, each of $R^3$ is independently selected from hydrogen, deuterium and $C_{1-6}$ alkyl.

The present disclosure also provides a pharmaceutical composition comprising any compound disclosed herein or a pharmaceutically acceptable salt, ester, isomer, solvate, prodrug or isotopically labeled compound thereof.

The present disclosure also provides a use of any compound disclosed herein, or a pharmaceutically acceptable salt, ester, isomer, solvate, prodrug or isotopically labeled compound thereof, or a pharmaceutical composition thereof in the preparation of medicament for the prophylaxis and/or treatment of diseases mediated at least in part by elastase, preferably in the preparation of medicament for the prophylaxis and/or treatment of chronic obstructive pneumonia.

The present disclosure also provides any compound disclosed herein or a pharmaceutically acceptable salt, ester, isomer, solvate, prodrug or isotopically labeled compound thereof, or the above said pharmaceutical composition thereof, for use as a medicament for the prophylaxis and/or treatment of diseases mediated at least in part by elastase, preferably for use as a medicament for the prophylaxis and/or treatment of chronic obstructive pulmonary disease.

The present disclosure also provides a method of preventing and/or treating a disease mediated at least in part by elastase, comprising a step of administering to a subject in need thereof a therapeutically effective amount of any compound disclosed herein, or a pharmaceutically acceptable salt, ester, isomer, solvate, prodrug or isotopically labeled compound thereof, or a pharmaceutical composition thereof.

Beneficial Effects of the Disclosure

Compared with the compound 52 (control example) in WO 2018/175173 A1, the compound disclosed herein has the advantages of high pulmonary exposure and long half-life. The prodrugs of the present disclosure significantly increase the concentration and residence time of the active compound (control example) in the lungs with significant improvements in pharmacokinetics in vivo compared to the control example.

DETAILED DESCRIPTION OF THE DISCLOSURE

Figure 1:
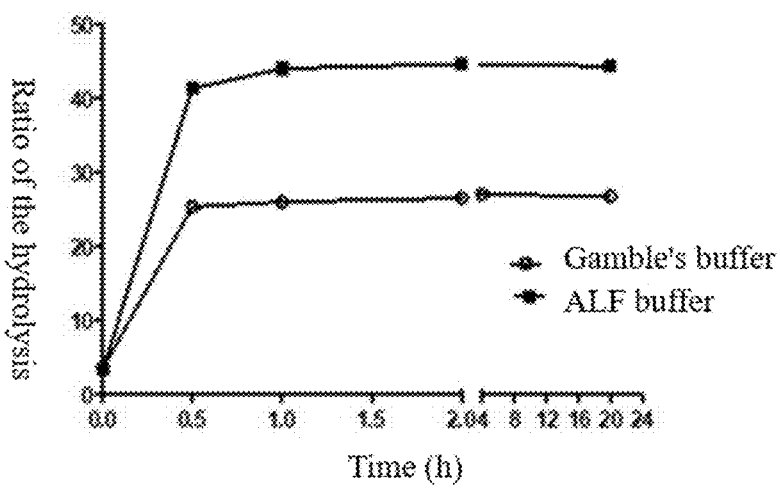
FIG. 1 shows the stability data of the compound of Example 1 in simulated lung fluid at 37° C.

To describe the content of the disclosure more clearly, the terms used in this application are defined as follows:

The term "$C_{1-6}$", alone or in combination, refers to a saturated straight chain or branched chain alkyl groups having 1 to 6 carbon atoms, preferably 1 to 4 carbon atoms, including methyl, ethyl, n-propyl, iso-propyl, butyl, sec-butyl, isobutyl, tert-butyl, n-pentyl, 2-pentyl, 3-pentyl, 2-methyl-2-butyl, 3-methyl-2-butyl, 3-methyl-1-butyl, 2-methyl-1-butyl, n-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, and the like. Preferably, "$C_{1-6}$ alkyl" is selected from any one of methyl, ethyl, iso-propyl and tert-butyl.

The term "$C_{3-8}$ cycloalkyl", alone or in combination, refers to a saturated cycloalkyl having 3 to 8 carbon atoms, in particular 5 to 7 carbon atoms, including monocyclic, bicyclic, bridged and spirocyclic cycloalkyl. Specifically, the monocyclic cycloalkyl includes cyclopropyl, cyclobutyl, cyclopentyl, cyclohexyl, cycloheptyl, cyclooctyl, and the like; the bicyclic cycloalkyl includes bicyclo[2.2.0]hexyl, bicyclo[3.1.0]hexyl, bicyclo[3.2.0]heptyl, bicyclo[3.3.0]octyl, bicyclo[4.1.0]heptyl, bicyclo[4.2.0]octyl, and the like; the bridged cycloalkyl includes bicyclo[2.2.1]heptyl, bicyclo[2.2.2]octyl, bicyclo[3.1.1]heptyl, bicyclo[3.2.1]octyl, bicyclo[4.1.1]octyl, and the like; the spiro ring includes spiro[2.2]pentyl, spiro[2.3]hexyl, spiro[3.3]heptyl, spiro[2.4]heptyl, spiro[3.4]octyl, spiro[2.5]octyl. In particular, "$C_{5-8}$ cycloalkyl" is any one of bicyclo[2.2.2]octyl and bicyclo[3.1.1]heptyl.

The term "$C_{1-6}$ alkoxy", alone or in combination, refers to $C_{1-6}$ alkyl-O—, wherein the "$C_{1-6}$ alkyl" is as defined above.

The term "amino", alone or in combination, refers to a primary amino group (—NH$_2$), a secondary amino group (—NH—) or a tertiary amino group

The term "hydroxyl", alone or in combination, refers to an —OH group.

The term "Halogen", alone or in combination, refers to fluorine, chlorine, bromine or iodine, in particular, fluorine, chlorine or bromine.

The term "isomer" means all isomeric forms, including enantiomers, diastereomers and geometric isomers (including cis-/trans-isomers). Therefore, the specific stereoisomeric forms of the compounds of the present disclosure or mixtures of enantiomers, diastereomers or geometric isomers (or cis-/trans-isomers) thereof are within the scope of the present disclosure.

The term "pharmaceutically acceptable salt(s)" refers to the existing form of pharmaceutically acceptable salt of the compound of the disclosure, including acid addition salt and base addition salt. Pharmaceutically acceptable salt(s) are described by S. M. Berge et al. in J. Pharmaceutical Sciences (Vol. 66, p. 1-19, 1977) in the section "Pharmaceutical salts". In the present disclosure, pharmaceutically acceptable non-toxic acid addition salts are those formed with organic or inorganic acids, including but not limited to hydrochloric acid, sulfuric acid, hydrobromic acid, hydroiodic acid, phosphoric acid, nitric acid, perchloric acid, acetic acid, oxalic acid, maleic acid, fumaric acid, tartaric acid, benzenesulfonic acid, methanesulfonic acid, salicylic acid, succinic acid, citric acid, lactic acid, propionic acid, benzoic acid, p-toluenesulfonic acid and malic acid, and the like. A pharmaceutically acceptable non-toxic base addition salt refers to a salt formed by a compound disclosed herein with an organic or inorganic base, including but not limited to alkali metal salt such as lithium, sodium or potassium salt; alkaline earth metal salt such as calcium or magnesium salt; organic base salt, such as ammonium salt or N+(C$_{1-6}$ alkyl)$_4$ salt formed with organic base having nitrogen-containing group(s). "Pharmaceutically acceptable salt(s)" can be synthesized by conventional chemical methods.

The term "ester" means an ester derived by reacting one or more hydroxyl groups in a compound of the present disclosure with one or more protic acids selected from carboxylic acid, phosphoric acid, carbonic acid, sulfonic acid and boric acid, and the like, or by reacting one or more carboxyl groups in a compound of the present disclosure with alcohols and/or phenols.

The term "solvate" refers to an association of one or more solvent molecules with a compound of the present disclosure, wherein solvent molecules include, but are not limited to, water, methanol, ethanol, isopropanol, ethyl acetate, tetrahydrofuran, N,N-dimethylformamide, dimethyl sulfoxide, and the like.

The term "hydrate" refers to the association of water with a compound of the present disclosure.

The term "prodrug" refers to a derivative of a compound of the present disclosure that can be transformed in vivo to the formula I compound by a chemical reaction.

The term "isotopically labeled compound" refers to isotopic derivatives derived by substituting 1 to 6 deuterium atoms for hydrogen atoms in the compound of the present disclosure and/or isotopes derived by replacing carbon atoms in the compound of the present disclosure with 1 to 3 $^{14}$C atoms.

The terms used in the present disclosure are as defined above, and those skilled in the art can also combined those with the prior art, and the content of the present disclosure is further described below based on the definitions.

The present disclosure provides a compound of formula I or a pharmaceutically acceptable salt, ester, isomer, solvate, prodrug or isotopically labeled compound thereof,

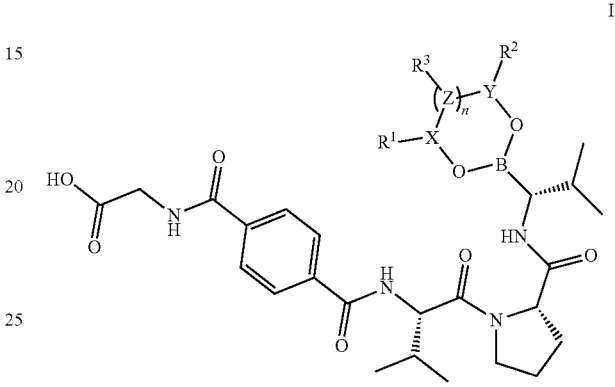

wherein:
when n is 0,
X and Y are directly connected, X and Y are CR$^4$ and CR$^5$ respectively;
R$^4$ and R$^5$ are each independently selected from hydrogen, deuterium and C$_{1-6}$ alkyl;
R$^1$ and R$^2$ are each independently selected from hydrogen, deuterium, halogen, C$_{1-6}$ alkyl and C$_{3-8}$ cycloalkyl, or R$^1$ and R$^2$ are connected to form a C$_{3-8}$ cycloalkane which is unsubstituted or substituted with one or more R$^6$;
If present, each of R$^6$ is independently selected from hydrogen, deuterium, hydroxy, amino, halogen, C$_{1-6}$ alkyl, halogen-substituted C$_{1-6}$ alkyl and C$_{1-6}$ alkoxy;
Or, when n is an integer from 1 to 5,
X—R$^1$ and Y—R$^2$ are each independently selected from carbonyl and CHR$^7$;
If present, each of R$^7$ is independently selected from hydrogen, deuterium and C$_{1-6}$ alkyl;
Each of Z is independently selected from O, S, CH and N, and when Z is O or S, R$^3$ to which it is attached is absent.
If present, each of R$^3$ is independently selected from hydrogen, deuterium and C$_{1-6}$ alkyl.

In one preferred embodiment, when n is 0, X and Y are directly connected, X and Y are CR$^4$ and CR$^5$ respectively, R$^4$ and R$^5$ are each independently selected from hydrogen, deuterium and C$_{1-6}$ alkyl, R$^1$ and R$^2$ are connected to form a C$_{5-8}$ cycloalkyl which is unsubstituted or substituted with one or more R$^6$, and C$_{5-8}$ cycloalkyl includes monocyclic, bicyclic, bridged and spirocyclic cycloalkyl.

In one preferred embodiment, when n is 0, X and Y are directly connected, X and Y are CR$^4$ and CR$^5$ respectively, R$^4$ and R$^5$ are each independently selected from hydrogen, deuterium, methyl and ethyl, R$^1$ and R$^2$ are connected to form a C$_{5-8}$ cycloalkyl which is unsubstituted or substituted with one or more R$^6$, and C$_{5-8}$ cycloalkyl is

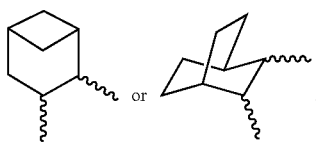 or ,

In one preferred embodiment, when n is 0, X and Y are directly connected, X and Y are CR$^4$ and CR$^5$ respectively, R$^4$ and R$^5$ are each independently selected from hydrogen, deuterium and C$_{1-6}$ alkyl, R$^1$ and R$^2$ are connected to form a C$_{5-8}$ cycloalkyl which is unsubstituted or substituted with 1 or 2 R$^6$, if present, each of R$^6$ is independently selected from hydrogen, deuterium, hydroxy, amino, fluorine, chlorine, bromine, methyl, ethyl, n-propyl, iso-propyl, fluoromethyl, difluoromethyl, trifluoromethyl, methoxy and ethoxy.

In one more preferred embodiment, when n is 0, X and Y are directly connected, X and Y are CR$^4$ and CR$^5$ respectively, R$^4$ and R$^5$ are each independently selected from hydrogen and methyl, and R$^1$ and R$^2$ are connected to form a C$_{5-8}$ cycloalkyl which is substituted with 1 or 2 R$^6$, and C$_{5-8}$ cycloalkyl is

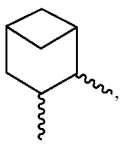,

R$^6$ is methyl.

In one preferred embodiment, when n is 0, X and Y are directly connected, X and Y are CR$^4$ and CR$^5$ respectively, R$^4$ and R$^5$ are each independently selected from hydrogen, deuterium, methyl and ethyl, R$^1$ and R$^2$ are each independently selected from hydrogen, deuterium, halogen, C$_{1-6}$ alkyl and C$_{3-8}$ cycloalkyl.

In one preferred embodiment, when n is 0, X and Y are directly connected, X and Y are C R$^4$ and CR$^5$ respectively, R$^4$ and R$^5$ are each independently selected from hydrogen, deuterium, methyl and ethyl, R$^1$ and R$^2$ are each independently selected from hydrogen, deuterium, fluorine, chlorine, bromine, methyl, ethyl, n-propyl, isopropyl, cyclopropyl, cyclobutyl, cyclopentyl and cyclohexyl.

In one preferred embodiment, when n is 0, X and Y are directly connected, X and Y are C R$^4$ and CR$^5$ respectively, R$^4$ and R$^5$ are each independently selected from hydrogen and methyl, R$^1$ and R$^2$ are each independently selected from hydrogen, fluorine, methyl and cyclopropyl.

In one preferred embodiment, when n is an integer of 1 to 5, X—R$^1$ and Y—R$^2$ are both carbonyl.

In one preferred embodiment, when n is an integer from 1 to 5, each of Z is independently selected from CH and N, and each of R$^3$ is independently selected from hydrogen, deuterium, methyl, ethyl, n-propyl and iso-propyl.

In one preferred embodiment, n is 3, X—R$^1$ and Y—R$^2$ are both carbonyl, and each of Z—R$^3$ is independently selected from methylene (—CH$_2$—) and N-methyl secondary amino (—N(CH$_3$)—), or n is 1, and Z—R$^3$ is methylene.

In one preferred embodiment,

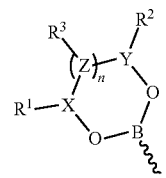

is

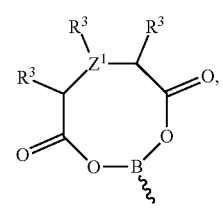

wherein Z$^1$ is O, S or N; when Z$^1$ is O or S, R$^3$ to which it is attached is absent, and each of the remaining R$^3$ is independently selected from hydrogen, deuterium, methyl and ethyl; when Z$^1$ is N, each of R$^3$ is independently selected from hydrogen, deuterium, methyl and ethyl.

In one preferred embodiment, when n is 0,
X and Y are directly connected, X and Y are CR$^4$ and CR$^5$ respectively,
R$^4$ and R$^5$ are each independently selected from hydrogen, deuterium, methyl and ethyl, preferably hydrogen and methyl;
R$^1$ and R$^2$ are each independently selected from hydrogen, deuterium, halogen, C$_{1-6}$ alkyl and C$_{3-8}$ cycloalkyl, preferably methyl,
Or, R$^1$ and R$^2$ are connected together to form a C$_{5-8}$ cycloalkyl which is unsubstituted or substituted with one or more, preferably 1 or 2 R$^6$, and C$_{5-8}$ cycloalkyl is

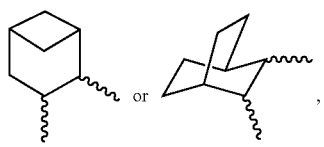 or , preferably;

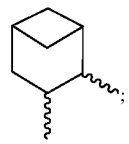;

If present, each of R$^6$ is independently selected from hydrogen, deuterium, methyl and ethyl, preferably methyl;
Or, when n is 3,
X—R$^1$ and Y—R$^2$ are both carbonyl;
Each of Z—R$^3$ is independently selected from methylene and N-methyl secondary amino.

The present disclosure also provides a compound or a pharmaceutically acceptable salt, ester, isomer, solvate, prodrug or isotopically labeled compound thereof, the compound is as follows:

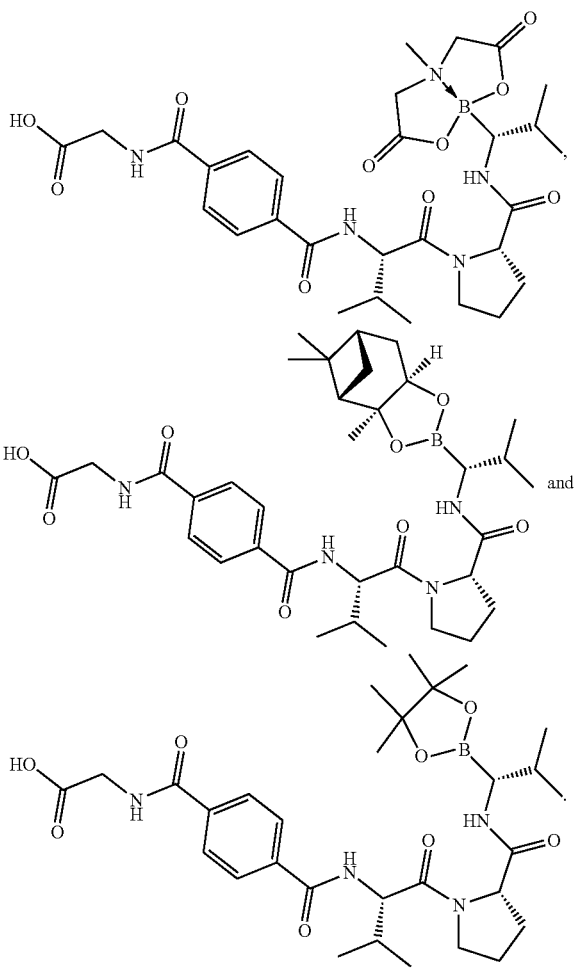

The present disclosure also provides a pharmaceutical composition comprising any compound disclosed herein or a pharmaceutically acceptable salt, ester, isomer, solvate, prodrug or isotopically labeled compound thereof.

The present disclosure also provides a use of any compound disclosed herein, or a pharmaceutically acceptable salt, ester, isomer, solvate, prodrug or isotopically labeled compound thereof, or a pharmaceutical composition thereof in the preparation of medicament for the prophylaxis and/or treatment of diseases mediated at least in part by elastase, preferably in the preparation of medicament for the prophylaxis and/or treatment of chronic obstructive pneumonia.

The present disclosure also provides any compound disclosed herein or a pharmaceutically acceptable salt, ester, isomer, solvate, prodrug or isotopically labeled compound thereof, or the above said pharmaceutical composition thereof, for use as a medicament for the prophylaxis and/or treatment of diseases mediated at least in part by elastase, preferably for use as a medicament for the prophylaxis and/or treatment of chronic obstructive pulmonary disease.

The present disclosure also provides a method of preventing and/or treating a disease mediated at least in part by elastase, comprising a step of administering to a subject in need thereof a therapeutically effective amount of any compound disclosed herein, or a pharmaceutically acceptable salt, ester, isomer, solvate, prodrug or isotopically labeled compound thereof, or a pharmaceutical composition thereof.

The technical scheme of the present disclosure is further described by a typical synthetic route of the compound of formula I, which is specifically shown below:

Compound 1 reacts with 2 to afford product 3;

Product 3 gives product 4 after alkali hydrolysis;

Product 4 and compound 5 are subjected to a condensation reaction to afford product 6;

Product 6 gives product 7 by subjecting a deprotection reaction;

Product 7 and compound 8 are subjected to a condensation reaction to afford product 9;

Product 9 gives product 10 after alkali hydrolysis.

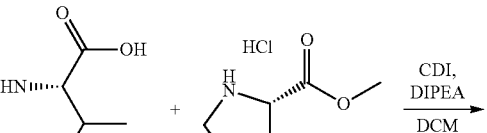

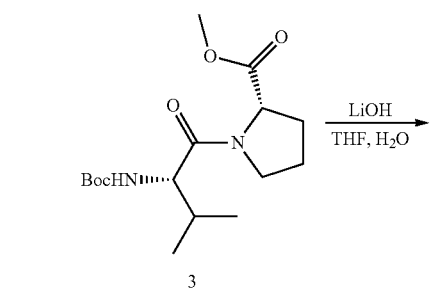

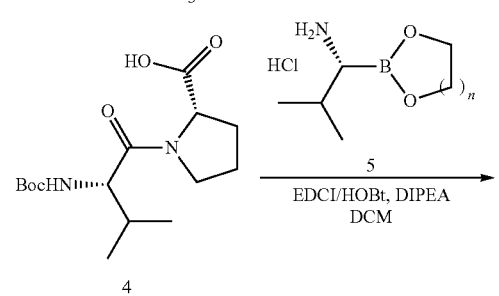

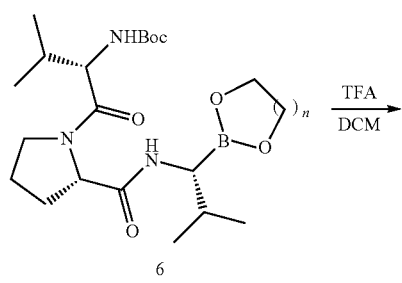

11
-continued
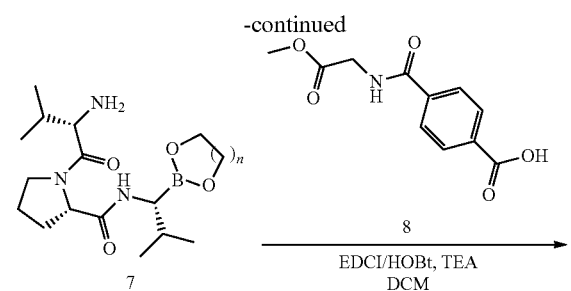
12
-continued
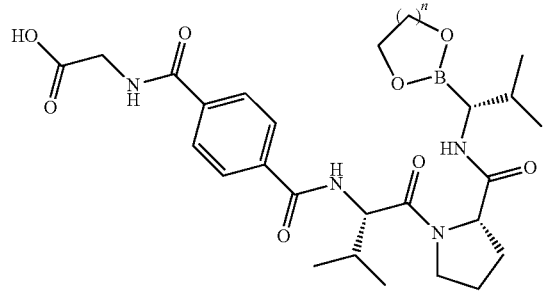
wherein n is an integer from 1 to 3.
As a variation of the above typical synthetic route, another reaction route is shown below:
Compound 10 gives product 11 by subjecting a deprotection reaction;
Product 11 reacts with compound 12 to obtain product 13.
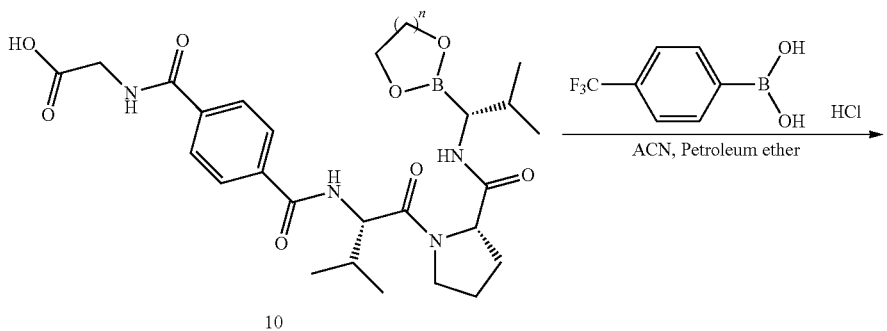
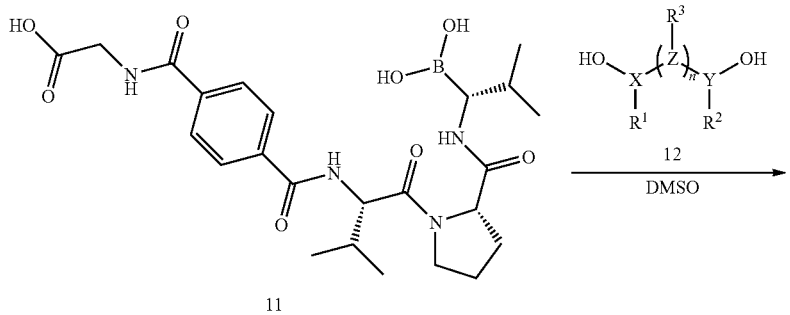
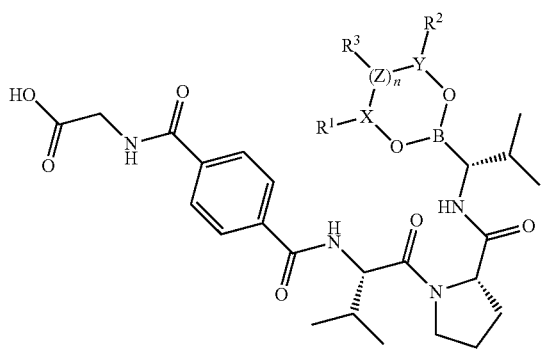

wherein n is an integer from 1 to 3, and X—R¹, Y—R² and Z—R³ are as defined above.

The following examples serve to illustrate the disclosure, but the examples should not be considered as limiting the scope of the present disclosure.

The following abbreviations are used in this application:
ACN is acetonitrile,
CDCl₃ is deuterated trichloromethane,
CDI: N,N'-carbonyldiimidazole,
CD₃OD is deuterated methanol,
DIPEA is N,N-diisopropylethylamine,
DCM is dichloromethane,
DMSO is dimethyl sulfoxide,
DMSO-d₆ is deuterated dimethyl sulfoxide
EDCI is 1-ethyl-(3-dimethylaminopropyl)carbodiimide hydrochloride
ESI is electrospray ionization source
HCOOH is formic acid,
¹H-NMR is hydrogen nuclear magnetic resonance spectroscopy,
HPLC is high performance liquid chromatography,
HOBt is 1-hydroxybenzotriazole,
Hz is hertz,
H₂O is water,
LC-MS is liquid chromatography-mass spectrometry,
LiOH is lithium hydroxide,
MHz is megahertz,
MS is mass spectrometry,
NMR is nuclear magnetic resonance,
Petroleum ether is petroleum ether,
TEA is triethylamine,
TFA is trifluoroacetic acid,
THF is tetrahydrofuran.

Specific conditions for the experimental method in the examples of the present disclosure are generally as follows:

First, unless otherwise stated in the examples, the following reactions were placed under nitrogen atmosphere.

Further, intermediates and final compounds were separated and purified by column chromatography, preparative chromatography and ICSO rapid preparative chromatography system.

Further, the LC-MS chromatograph was generally performed on Waters ACQUITY Arc equipped with QDa Detector. Mass spectrometry (MS) uses an ESI source and only indicates the molecular weight M of the parent molecule, usually reporting [M+H]⁺.

Injection volume was determined by sample concentration; flow rate: 0.8 mL/min; HPLC peaks were read by recording UV-Vis wavelengths at 220 nm and 254 nm.

The mobile phases were 0.01% formic acid in ultrapure water (mobile phase A) and 0.01% formic acid in acetonitrile (mobile phase B). The gradient elution conditions are shown in the following Table 1 and Table 2:

TABLE 1

| gradient elution condition 1 | | |
|---|---|---|
| Time(min) | A(H₂O, 0.01% HCOOH) | B(CH₃CN, 0.01% HCOOH) |
| 0.0-0.3 | 95-85 | 5-15 |
| 0.3-3.2 | 85-20 | 15-80 |
| 3.2-3.8 | 20-5 | 80-95 |
| 3.8-3.81 | 5-95 | 95-5 |
| 3.81-4.0 | 95 | 5 |

TABLE 2

| gradient elution condition 2 | | |
|---|---|---|
| Time(min) | A(H₂O, 0.01% HCOOH) | B(CH₃CN, 0.01% HCOOH) |
| 0.00-5.90 | 95-5 | 5-95 |
| 5.90-5.91 | 5-95 | 95-5 |
| 5.91-6.00 | 95 | 5 |

Further, NMR spectra were obtained using a Varian 400 MHz nuclear magnetic resonance. The solvents were usually CDCl₃ and DMSO-d₆, and the chemical shifts were given in ppm. The various peaks are described as follows: s (singlet), d (doublet), t (triplet), q (quartet), m (multiplet), dd (doublet doublet). Coupling constants are indicated in Hz.

EXAMPLE 1

N-(4-(((S)-3-methyl-1-((S)-2-(((R)-2-methyl-1-((3aS,4S,6S,7aR)-3a,5,5-trimethylhexahydro-4,6-methanobenzo[d][1,3,2]dioxaborol-2-yl)propyl)carbamoyl)pyrrolidin-1-yl)-1-oxobutan-2-yl)carbamoyl) benzoyl)glycine Step 1a Methyl N—(N-tert-butoxycarbonyl)-L-valyl-L-prolinate

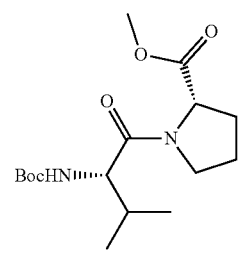 [SMILES: COC(=O)[C@@H]1CCCN1C(=O)[C@@H](NC(=O)OC(C)(C)C)C(C)C]

N-tert-butoxycarbonyl-L-valine (55.0 g), L-proline methyl ester hydrochloride (46.1 g), N,N-diisopropylethylamine (59.5 g) and N,N'-carbonyldiimidazole (43.1 g) were dissolved in dichloromethane (200 mL) in a nitrogen atmosphere and stirred at room temperature for 6 hours, and HPLC showed the reaction was complete. The reaction solution was washed with sodium bicarbonate solution, dilute hydrochloric acid and water respectively. The organic layer was concentrated under reduced pressure by removing the solvent to afford an intermediate methyl N—(N-tert-butoxycarbonyl)-L-valyl-L-prolinate (72.0 g) as a pale yellow oil.

Step 1b

N—(N-tert-butoxycarbonyl)-L-valyl-L-proline

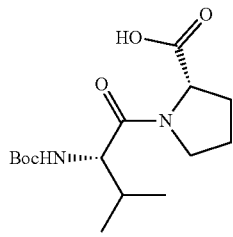 [SMILES: CC(C)[C@H](NC(=O)OC(C)(C)C)C(=O)N1CCC[C@H]1C(=O)O]

The intermediate N—(N-tert-butoxycarbonyl-L-valyl)-L-proline methyl ester (72.0 g) and lithium hydroxide (18.4 g) were dissolved in tetrahydrofuran (360 mL) and water (120 mL) in a nitrogen atmosphere and stirred at room temperature for 3 hours. HPLC showed the reaction was complete, and then sodium hydroxide solution (2 wt %, 350 mL) was added to the reaction solution, and the reaction solution was washed with ethyl acetate. The aqueous phase was adjusted to pH 3-4 with hydrochloric acid, and then extracted with ethyl acetate. The organic phases were combined and concentrated under reduced pressure. Ethyl acetate (10 mL) and n-heptane (400 mL) were added to the crude product, and stirred at room temperature for 5 hours, and filtered. The filter cake was rinsed with n-heptane (50 mL), and dried under reduced pressure to afford an intermediate N—(N-tert-butoxycarbonyl)-L-valyl-L-proline (59.6 g) as a white solid.

Step 1c

Tert-butyl ((S)-3-methyl-1-((S)-2-(((R)-2-methyl-1-((3aS,4S,6S,7aR)-3a,5,5-trimethylhexahydro-4,6-methanobenzo[d][1,3,2]dioxaborol-2-yl)propyl)carbamoyl)pyrrolidin-1-yl)-1-oxobutan-2-yl)carbamate

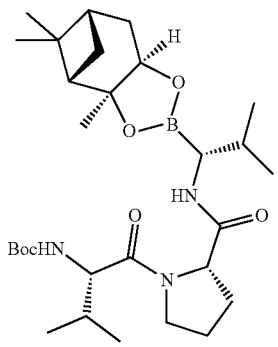 [SMILES: CC(C)[C@H](NC(=O)[C@@H]1CCCN1C(=O)[C@@H](NC(=O)OC(C)(C)C)C(C)C)B1O[C@@H]2C[C@@H]3C[C@@H](C3(C)C)[C@]2(C)O1]

The intermediate N—(N-tert-butoxycarbonyl-L-valyl)-L-proline (15.0 g), (R)-2-methyl-1-((3aS,4S,6S,7aR)-3a,5,5-trimethylhexahydro-4,6-methylbenzo[d][1,3,2]dioxaboran-2-yl)propyl-1-amine (17.8 g), 1-(3-dimethylaminopropyl)-3-ethylcarbodiimide hydrochloride (11.9 g) and 1-hydroxybenzotriazole (8.4 g) were dissolved in dichloromethane (300 mL) in a nitrogen atmosphere and N,N-diisopropylethylamine (24.7 g) was slowly added dropwise at room temperature, then the temperature was raised to reflux, and stirred for 6 hours. HPLC showed the reaction was complete. The reaction solution was washed with sodium bicarbonate solution, dilute hydrochloric acid and water, and then was concentrated under reduced pressure by removing the solvent to afford an intermediate tert-butyl ((S)-3-methyl-1-((S)-2-(((R)-2-methyl-1-((3aS,4S,6S,7aR)-3a,5,5-trimethylhexahydro-4,6-methanobenzo[d][1,3,2]dioxaborol-2-yl)propyl)carbamoyl)pyrrolidin-1-yl)-1-oxobutan-2-yl)carbamate (27.04 g).

Step 1d (S)-1-(L-valyl)-N—((R)-2-methyl-1-((3aS,4S,6S,7aR)-3a,5,5-trimethylhexahydro-4,6-methanobenzo[d][1,3,2]dioxaborol-2-yl)propyl)pyrrolidine-2-carboxamide

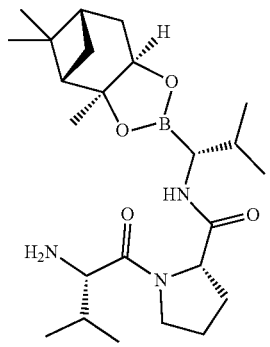 [SMILES: CC(C)[C@H](NC(=O)[C@@H]1CCCN1C(=O)[C@@H](N)C(C)C)B1O[C@@H]2C[C@@H]3C[C@@H](C3(C)C)[C@]2(C)O1]

The intermediate tert-butyl ((S)-3-methyl-1-((S)-2-(((R)-2-methyl-1-((3aS,4S,6S,7aR)-3a,5,5-trimethylhexahydro-4,6-methanobenzo[d][1,3,2]dioxaborol-2-yl)propyl)carbamoyl)pyrrolidin-1-yl)-1-oxobutan-2-yl)carbamate (34.62 g) was dissolved in dichloromethane (300 mL) in a nitrogen atmosphere, cooled to 0° C., trifluoroacetic acid (60 mL) was slowly added dropwise, and then stirred for 6 hours. HPLC showed the reaction was complete, and was concentrated under reduced pressure to remove the solvent, then dichloromethane (200 mL) was added, adjusted the pH to 9 with sodium bicarbonate solution, allowed for separation, the aqueous phase was extracted with dichloromethane, the combined organic phases were washed with water, and was concentrated under reduced pressure to remove the solvent to afford an intermediate (S)-1-(L-valyl)-N—((R)-2-methyl-1-((3aS,4S,6S,7aR)-3a,5,5-trimethylhexahydro-4,6-methanobenzo[d][1,3,2]dioxaborol-2-yl)propyl)pyrrolidine-2-carboxamide (30.9 g) as a light yellow oil.

Step 1e

Methyl N-(4-(((S)-3-methyl-1-((S)-2-(((R)-2-methyl-1-((3aS,4S,6S,7aR)-3a,5,5-trimethylhexahydro-4,6-methanobenzo[d][1,3,2]dioxaborol-2-yl)propyl)carbamoyl)pyrrolidin-1-yl)-1-oxobutan-2-yl)carbamoyl)benzoyl)glycinate The intermediate (S)-1-(L-valyl)-N—((R)-2-methyl-1-((3aS,4S,6S,7aR)-3a,5,5-trimethylhexahydro-4,6-methanobenzo[d][1,3,2]dioxaborol-2-yl)propyl)pyrrolidine-2-carboxamide (30.9 g), 4-((2-methoxy-2-oxoethyl)carbamoyl)benzoic acid (18.0 g) was dissolved in dichloromethane (300 mL) in a nitrogen atmosphere, triethylamine (31.4 g) was slowly added dropwise at room temperature, and then 1-(3-dimethylaminopropyl)-3-ethylcarbodiimide hydrochloride (15.8 g) and 1-hydroxybenzotriazole (11.1 g) were added, then heated to reflux and stirred for 6 hours. HPLC showed the reaction was complete. The reaction solution was washed successively with sodium bicarbonate solution, dilute hydrochloric acid and water. The solvent was removed by concentration under reduced pressure. The crude product was purified by column chromatography to afford methyl N-(4-(((S)-3-methyl-1-((S)-2-(((R)-2-methyl-1-((3aS,4S,6S,7aR)-3a,5,5-trimethylhexahydro-4,6-methanobenzo[d][1,3,2]dioxaborol-2-yl)propyl)carbamoyl)pyrrolidin-1-yl)-1-oxobutan-2-yl)carbamoyl)benzoyl)glycinate as a white solid (21.1 g).

Step 1f

N-(4-(((S)-3-methyl-1-((S)-2-(((R)-2-methyl-1-((3aS,4S,6S,7aR)-3a,5,5-trimethylhexahydro-4,6-methanobenzo[d][1,3,2]dioxaborol-2-yl)propyl)carbamoyl)pyrrolidin-1-yl)-1-oxobutan-2-yl)carbamoyl)benzoyl)glycine

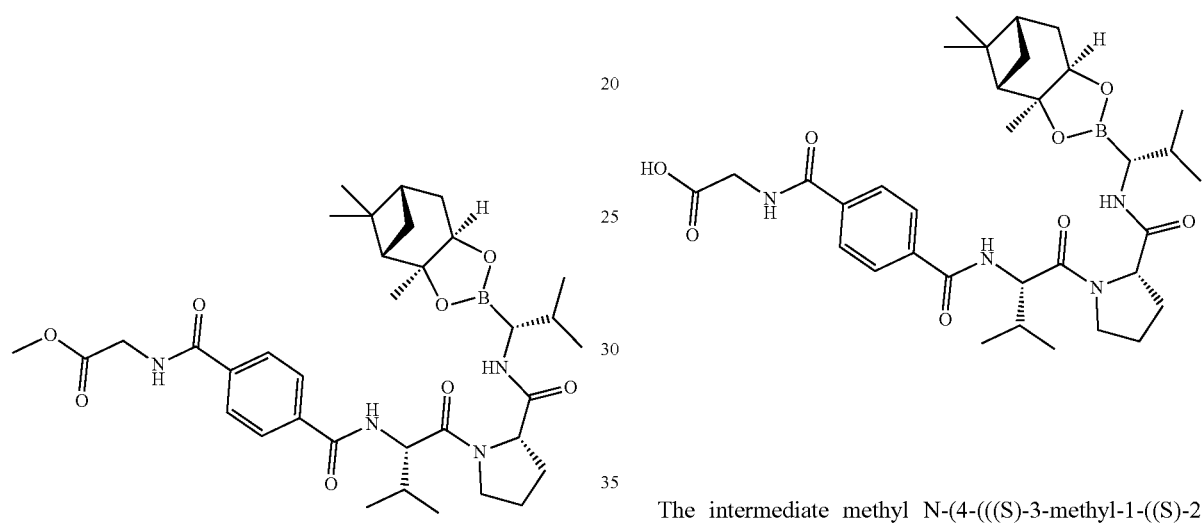

The intermediate methyl N-(4-(((S)-3-methyl-1-((S)-2-(((R)-2-methyl-1-((3aS,4S,6S,7aR)-3a,5,5-trimethylhexahydro-4,6-methanobenzo[d][1,3,2]dioxaborol-2-yl)propyl)carbamoyl)pyrrolidin-1-yl)-1-oxobutan-2-yl)carbamoyl)benzoyl)glycinate (2.44 g) and lithium hydroxide monohydrate (0.31 g) were dissolved in tetrahydrofuran (30 mL) and water (10 mL) in a nitrogen atmosphere, and stirred at room temperature for 2 hours. HPLC showed the reaction was complete. The reaction solution was concentrated, then water (15 mL) was added, and adjusted the pH of the solution to 4 with hydrochloric acid. The solution was extracted three times with dichloromethane (100 mL), and the combined organic phases were concentrated to obtain a crude product as a white solid. Ethyl acetate (2 mL) and n-heptane (10 mL) were added to the crude product, and stirred at room temperature for 5 hours, filtered and the filter cake was rinsed with n-heptane (5 mL), and dried under reduced pressure to afford N-(4-(((S)-3-methyl-1-((S)-2-(((R)-2-methyl-1-((3aS,4S,6S,7aR)-3a,5,5-trimethylhexahydro-4,6-methanobenzo[d][1,3,2]dioxaborol-2-yl)propyl)carbamoyl)pyrrolidin-1-yl)-1-oxobutan-2-yl)carbamoyl)benzoyl)glycine as a white solid (2.27 g), yield: 95.0%.

$^1$H-NMR (CD$_3$OD, 400 MHz) δ 7.89-7.98 (m, 4H), 4.57-4.66 (m, 2H), 4.15-4.21 (m, 1H), 4.02-4.11 (m, 3H), 3.75-3.83 (m, 1H), 2.49 (d, J=6.78 Hz, 1H), 2.02-2.36 (m, 7H), 1.95 (t, J=5.40 Hz, 1H), 1.77-1.88 (m, 3H), 1.50 (d, J=10.29 Hz, 1H), 1.34 (s, 3H), 1.28 (s, 3H), 1.08 (dd, J=11.04, 6.53 Hz, 6H), 0.95-1.02 (m, 7H), 0.85-0.89 (m, 3H).

MS (ESI$^+$)[(M+H)$^+$]: 653.

EXAMPLE 2

N-(4-(((S)-3-methyl-1-((S)-2-(((R)-2-methyl-1-(6-methyl-4,8-dioxo-1,3,6,2-dioxazaborocan-2-yl)propyl)carbamoyl)pyrrolidin-1-yl)-1-oxobutan-2-yl)carbamoyl)benzoyl)glycine

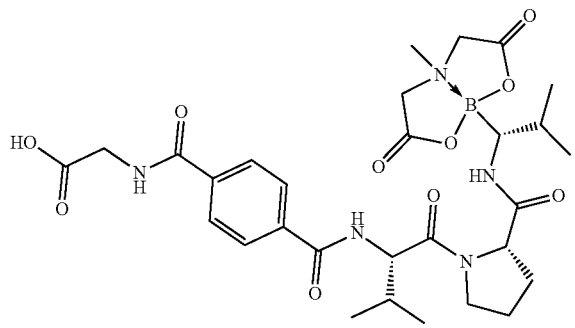 [SMILES: CC(C)[C@H](NC(=O)c1ccc(C(=O)NCC(=O)O)cc1)C(=O)N1CCC[C@H]1C(=O)N[C@@H](C(C)C)[B-]12OC(=O)C[N+]1(C)CC(=O)O2]

Step 2a

N-(4-(((S)-1-((S)-2-(((R)-1-borono-2-methylpropyl)carbamoyl)pyrrolidin-1-yl)-3-methyl-1-oxobutan-2-yl)carbamoyl)benzoyl)glycine

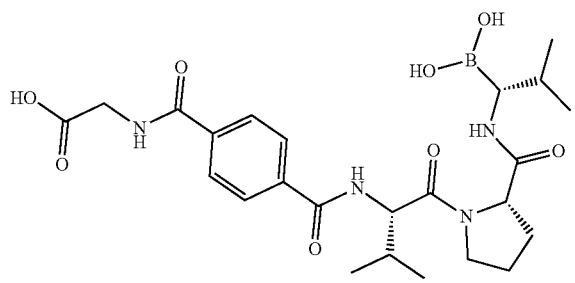 [SMILES: CC(C)[C@H](NC(=O)[C@@H]1CCCN1C(=O)[C@@H](NC(=O)c1ccc(C(=O)NCC(=O)O)cc1)C(C)C)B(O)O]

The intermediate N-(4-(((S)-3-methyl-1-((S)-2-(((R)-2-methyl-1-((3aS,4S,6S,7aR)-3a,5,5-trimethylhexahydro-4,6-methanobenzo[d][1,3,2]dioxaborol-2-yl)propyl)carbamoyl)pyrrolidin-1-yl)-1-oxobutan-2-yl)carbamoyl)benzoyl)glycine (7.4 g), 4-trifluoromethylphenylboronic acid (2.4 g) were dissolved in acetonitrile (100 mL) and petroleum ether (250 mL) in a nitrogen atmosphere, then concentrated hydrochloric acid (10 mL) was added and stirred at 60° C. for 4 hours, allowed for stratification, and the upper petroleum ether layer was separated, fresh petroleum ether (250 mL) was added, and continued to stir at 60° C. for 4 hours. HPLC showed the reaction was complete. The solution was allowed for stratification, and the acetonitrile layer was washed with petroleum ether. The solvent was removed by concentration under reduced pressure to afford a crude product. Tetrahydrofuran (50 mL) and ethyl acetate (300 mL) were added to the crude product and stirred at room temperature for 6 hours. The solution was filtered and the filter cake was washed with ethyl acetate (10 mL). Dried under reduced pressure to afford N-(4-(((S)-1-((S)-2-(((R)-1-borono-2-methylpropyl)carbamoyl)pyrrolidin-1-yl)-3-methyl-1-oxobutan-2-yl)carbamoyl)benzoyl)glycine (2.75 g) as a white solid, yield: 50.8%, purity: 99.0%.

Step 2b

N-(4-(((S)-3-methyl-1-((S)-2-(((R)-2-methyl-1-(6-methyl-4,8-dioxo-1,3,6,2-dioxazaborocan-2-yl)propyl)carbamoyl)pyrrolidine-1-yl)-1-oxobutan-2-yl)carbamoyl)benzoyl)glycine

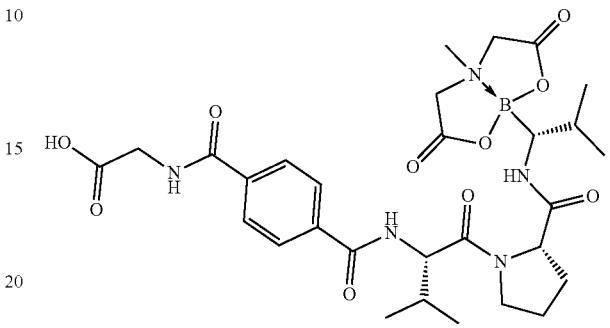

N-(4-(((S)-1-((S)-2-(((R)-1-borono-2-methylpropyl)carbamoyl)pyrrolidin-1-yl)-3-methyl-1-oxobutan-2-yl)carbamoyl)benzoyl)glycine (300 mg), N-methyliminodiacetic acid (102 mg) were dissolved in dimethylsulfoxide sulfone (2 mL) in a nitrogen atmosphere, then the temperature was raised to 120° C. and stirred for 10 hours. TLC showed the reaction was complete. The reaction solution was purified by reversed-phase column purification (gradient: 0.01% formic acid acetonitrile: 0.01% formic acid water, 0%~20%), lyophilized to afford N-(4-(((S)-3-methyl-1-((S)-2-(((R)-2-methyl-1-(6-methyl-4,8-dioxo-1,3,6,2-dioxazaborocan-2-yl)propyl)carbamoyl)pyrrolidine-1-yl)-1-oxobutan-2-yl)carbamoyl)benzoyl)glycine (70 mg) as a white solid, yield: 19%.

$^1$H-NMR (400 MHz, CD$_3$OD) δ 7.94 (s, 4H), 4.65-4.61 (m, 1H), 4.53-4.49 (m, 1H), 4.14-4.01 (m, 6H), 3.84 (s, 1H), 3.78-3.72 (m, 1H), 3.58 (dd, J=4.0 Hz, 12.0 Hz, 1H), 2.92 (s, 3H), 2.28-2.16 (m, 2H), 2.10-1.99 (m, 4H), 1.12-1.07 (m, 6H), 0.93 (dd, J=4.0 Hz, 8.0 Hz, 6H).

MS (ESI$^+$)[(M+H)$^+$]: 630.

EXAMPLE 3

N-(4-(((S)-3-methyl-1-((S)-2-(((R)-2-methyl-1-(4,4,5,5-tetramethyl-1,3,2-dioxaborolan-2-yl)propyl)carbamoyl)pyrrolidin-1-yl)-1-oxobutan-2-yl)carbamoyl)benzoyl)glycine

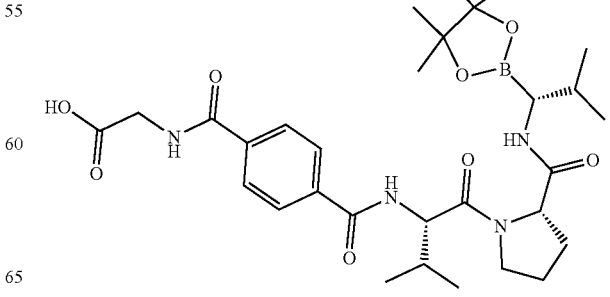

N-(4-(((S)-1-((S)-2-(((R)-1-borono-2-methylpropyl)carbamoyl)pyrrolidin-1-yl)-3-methyl-1-oxobutan-2-yl)carbamoyl)benzoyl)glycine (100 mg), pinacol (68 mg) were dissolved in dimethyl sulfoxide (0.5 mL) in a nitrogen atmosphere, and the temperature was raised to 120° C. and stirred for 6 hours. LC-MS showed the reaction was complete. After the reaction solution was lyophilized, the solid was dissolved in ethyl acetate and purified by thin layer chromatography, then lyophilized to afford N-(4-(((S)-3-methyl-1-((S)-2-(((R)-2-methyl-1-(6-methyl-4,8-dioxo-1,3,6,2-dioxazaborocan-2-yl)propyl)carbamoyl)pyrrolidine-1-yl)-1-oxobutan-2-yl)carbamoyl)benzoyl)glycine (45 mg) as a white solid, yield: 39%.

$^1$H-NMR (400 MHz, CD$_3$OD) δ 7.97-7.90 (m, 4H), 4.67-4.58 (m, 2H), 4.08 (br. s., 4H), 3.79 (d, J=6.44 Hz, 2H), 2.41 (d, J=6.19 Hz, 1H), 2.15-2.36 (m, 4H), 2.01-2.12 (m, 2H), 1.84 (td, J=13.21, 6.57 Hz, 2H), 1.14-1.25 (m, 12H), 1.10 (dd, J=15.21, 6.70 Hz, 6H), 1.01 (d, J=6.70 Hz, 2H), 0.91-0.98 (m, 4H).

MS (ESI$^+$)[(M+H)$^+$]: 601.

Stability Test:

Two simulated lung fluids including Gamble's buffer and ALF buffer were prepared according to literature reports (Marques M. R. C., Loebenberg R., Almukainzi M., Simulated Biological Fluids with Possible Application in Dissolution Testing, *Dissolution Technologies*, 2011, 18(3): 15-28) to test the prodrug stability in simulated lung fluids. In addition, according to the need for animal experimental preparations and sample analysis, three different solvents were prepared: vehicle for animal experiments (water with 5% ethanol), anhydrous ethanol and acetonitrile. They were used to test the stability of pre-dose formulations in animals and collected samples during analysis. Dissolve example 1 compound (2 mg) and example 2 compound (2 mg) in 1 mL of the above-filtered buffer or solvent, respectively. Observe whether there is undissolved particulate matter after vortex shaking, and then filter the suspension or solution to remove undissolved compounds and immediately take 100 μL as the sample at the start of the stability test. Then the ratio of prodrug and hydrolyzate (namely compound 52 in WO 2018/175173 A1, used as a control) was analyzed by HPLC.

Afterwards the samples in the two simulated lung fluids were placed on an orbital shaker at 37° C. and shaken at 200 rpm, and sampling at 0.5 hours, 1 hour, 2 hours, 4 hours and 20 hours, and the ratio of prodrug and hydrolyzate were analyzed by HPLC immediately. Let the samples dissolved in the three solvents stand at room temperature, sampling at 1 hour, 3 hours, and 18 hours, and the ratio of prodrug and hydrolyzate were immediately detected.

Figure 2:
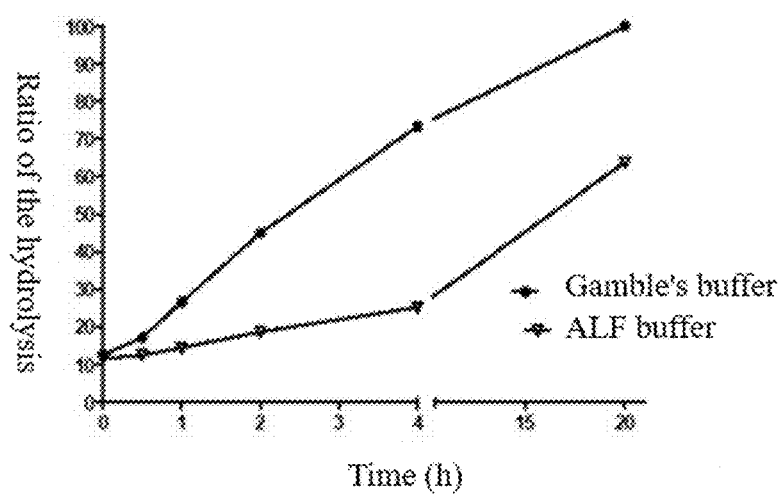
FIG. 2 shows the stability data of the compound of Example 2 in simulated lung fluid at 37° C.
Figure 3:
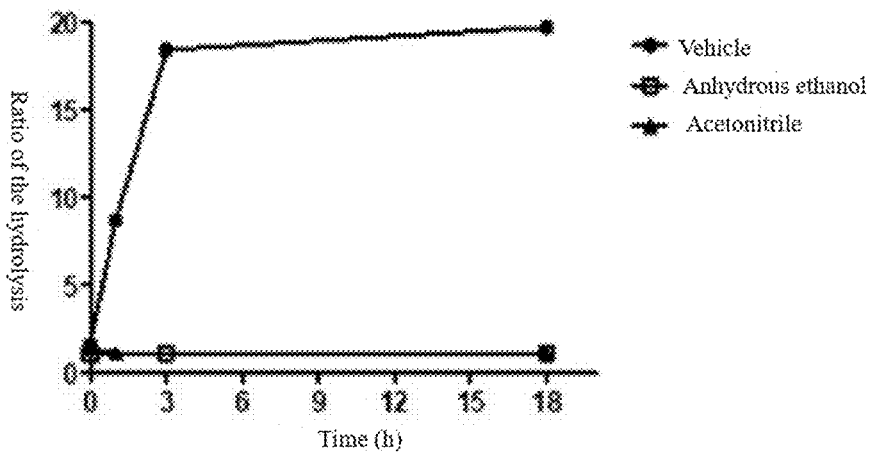
FIG. 3 shows the stability data of the compound of Example 1 in different solvents at room temperature.
Figure 4:
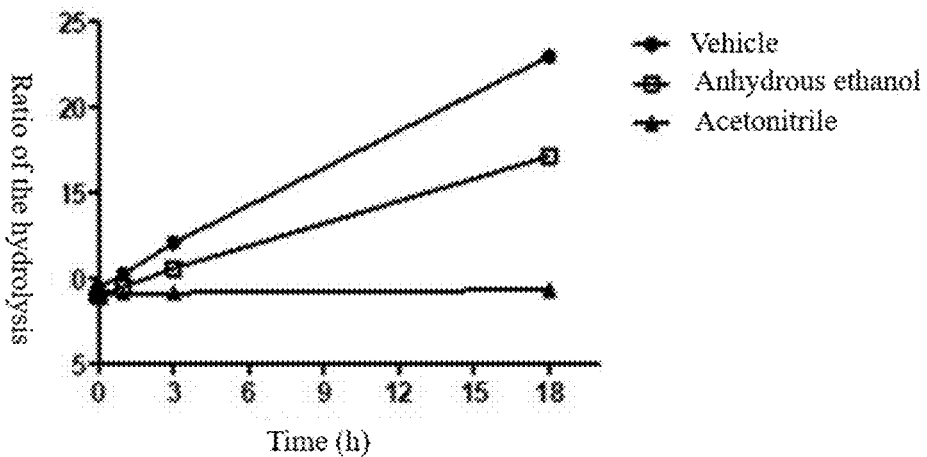
FIG. 4 shows the stability data of the compound of Example 2 in different solvents at room temperature.

Test Results:

Example 1 compound and Example 2 compound display distinct hydrolysis profiles and characteristics. As shown in FIG. 1, the ratio of the hydrolysis of Example 1 compound reached 25% and 40% respectively after which was dissolved in two simulated lung fluids, neutral Gamble's buffer (pH 7.4) and acidic ALF buffer (pH 4.5) within half an hour. And this ratio was maintained for the next 20 hours, that is, a stable equilibrium was reached. As shown in FIG. 2, the hydrolysis rate of the Example 2 compound is linear, with faster hydrolysis which was close to 50% hydrolysis at 2.5 hours in the neutral Gamble's buffer (pH 7.4), and with slightly slower hydrolysis which was about 50% in about 15 hours in the acidic ALF buffer (pH 4.5). As shown in FIG. 3, the Example 1 compound was hardly hydrolyzed in acetonitrile and anhydrous ethanol; whereas in the resolvent, the Example 1 compound was hydrolyzed by about 18% in 3 hours, and then the hydrolysis rate slowed down with about 20% hydrolyzed after 18 hours. As shown in FIG. 4, the hydrolysis rate of the Example 2 compound in three solvents also showed linear and stable, which did not hydrolyze in acetonitrile, and about 0.5% of the compound was hydrolyzed per hour in anhydrous ethanol, and in the resolvent, the hydrolysis rate is about 1% hydrolysis per hour.

In Vivo Pharmacokinetic Experiments:

Compare the pharmacokinetics of the final prodrug compound of Example 1 and the control example (compound 52 in WO 2018/175173 A1) in mice:

7-9-week-old male C57BL/6 mice were randomly divided into two groups after the adaptation phase: the elastase inhibitor control group and the Example 1 group. The details of administration are shown in Table 3.

TABLE 3

| Experimental design of pharmacokinetics in mice | | | | |
|---|---|---|---|---|
| Group | Compound | Number of animals | Administration | Dose |
| First Group | Control example | 4 | Intratracheal administration | 2 mg/kg |
| Second Group | Example 1 | 12 | Intratracheal administration | 2 mg/kg |

Figure 5:
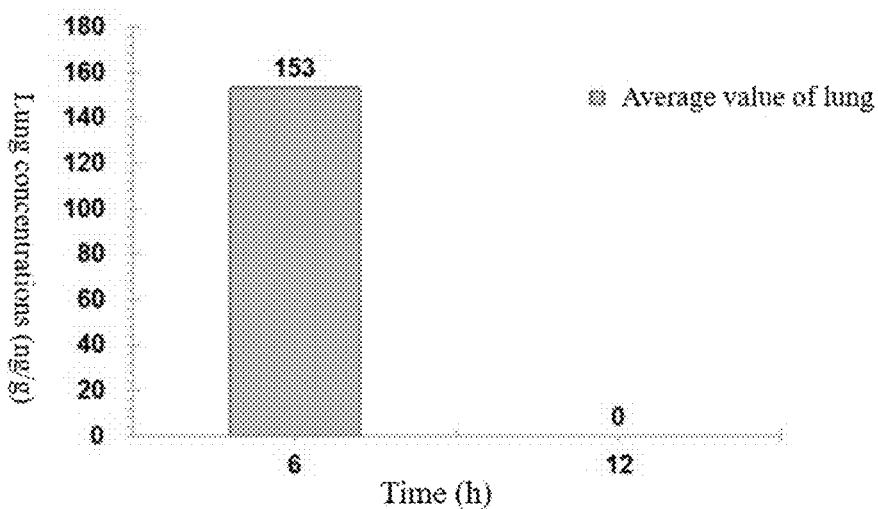
FIG. 5 shows the pulmonary drug concentration after intratracheal administration (2 mg/kg) of the control example in mice.
Figure 6:
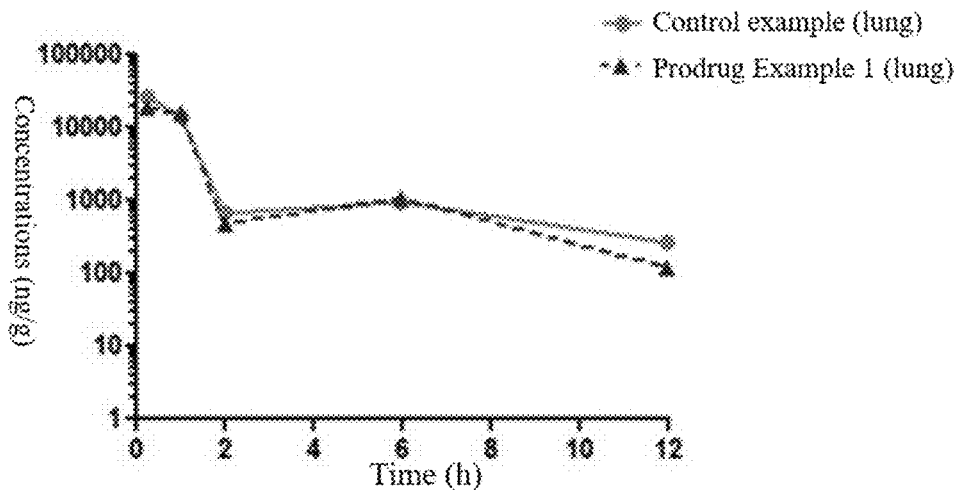
FIG. 6 shows the drug concentration of the compound of Example 1 and the hydrolysate (control example) in the lung after intratracheal administration (2 mg/kg) in mice.

Results of Pharmacokinetic Studies in Mice:

In the experimental results of pharmacokinetics in mice as shown in FIG. 5, the drug concentration of the control example in the lungs was 153 ng/g at 6 hours, and it was completely cleared at 12 hours. Whereas the Example 1 group, which is the prodrug of the control example, is quickly converted into the control example in mice. As shown in FIG. 6, the lung concentrations of prodrug Example 1 were 1070 ng/g and 120 ng/g at 6 hours and 12 hours, respectively, and the concentration of its hydrolysate (control example) which had inhibitory activity in the lungs was 931 ng/g at 6 hours and 264 ng/g at 12 hours. The results show that the prodrug Example 1 greatly increases the concentration and residence time of the control example in the lungs compared to the direct administration of the control example itself. The Example 1 compound had a significant improvement in in vivo PK relative to the control example.

The invention claimed is:

1. A compound of formula I or a pharmaceutically acceptable salt, ester, isomer, solvate, prodrug or isotopically labeled compound thereof,

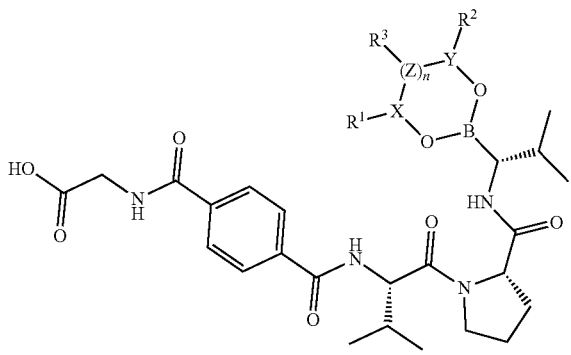

I wherein:
when n is 0,
X and Y are directly connected, X and Y are $CR^4$ and $CR^5$ respectively;
$R^4$ and $R^5$ are each independently selected from hydrogen, deuterium and $C_{1-6}$ alkyl;
$R^1$ and $R^2$ are each independently selected from hydrogen, deuterium, halogen, $C_{1-6}$ alkyl and $C_{3-8}$ cycloalkyl, or $R^1$ and $R^2$ are connected to form a $C_{3-8}$ cycloalkane which is unsubstituted or substituted with one or more $R^6$;
If present, each of $R^6$ is independently selected from hydrogen, deuterium, hydroxy, amino, halogen, $C_{1-6}$ alkyl, halogen-substituted $C_{1-6}$ alkyl and $C_{1-6}$ alkoxy;
Or, when n is an integer from 1 to 5,
X—$R^1$ and Y—$R^2$ are each independently selected from carbonyl and $CHR^7$;
If present, each of $R^7$ is independently selected from hydrogen, deuterium and $C_{1-6}$ alkyl;
Each of Z is independently selected from O, S, CH and N, and when Z is O or S, $R^3$ to which it is attached is absent,
If present, each of $R^3$ is independently selected from hydrogen, deuterium and $C_{1-6}$ alkyl.

2. The compound of formula I or a pharmaceutically acceptable salt, ester, isomer, solvate, prodrug or isotopically labeled compound thereof according to claim 1, wherein
when n is 0, X and Y are directly connected, X and Y are $CR^4$ and $CR^5$ respectively, $R^4$ and $R^5$ are each independently selected from hydrogen, deuterium and $C_{1-6}$ alkyl, $R^1$ and $R^2$ are connected to form a $C_{5-8}$ cycloalkyl which is unsubstituted or substituted with one or more $R^6$, and $C_{5-8}$ cycloalkyl includes monocyclic, bicyclic, bridged and spirocyclic cycloalkyl.

3. The compound of formula I or a pharmaceutically acceptable salt, ester, isomer, solvate, prodrug or isotopically labeled compound thereof according to claim 2, wherein
when n is 0, X and Y are directly connected, X and Y are $CR^4$ and $CR^5$ respectively, $R^4$ and $R^5$ are each independently selected from hydrogen, deuterium, methyl and ethyl, $R^1$ and $R^2$ are connected to form a $C_{5-8}$ cycloalkyl which is unsubstituted or substituted with one or more $R^6$, and $C_{5-8}$ cycloalkyl is

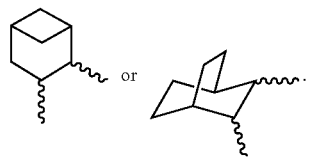

4. The compound of formula I or a pharmaceutically acceptable salt, ester, isomer, solvate, prodrug or isotopically labeled compound thereof according to claim 1, wherein
when n is 0, X and Y are directly connected, X and Y are $CR^4$ and $CR^5$ respectively, $R^4$ and $R^5$ are each independently selected from hydrogen, deuterium and $C_{1-6}$ alkyl, $R^1$ and $R^2$ are connected to form a $C_{5-8}$ cycloalkyl which is unsubstituted or substituted with 1 or 2 $R^6$, if present, each of $R^6$ is independently selected from hydrogen, deuterium, hydroxy, amino, fluorine, chlorine, bromine, methyl, ethyl, n-propyl, iso-propyl, fluoromethyl, difluoromethyl, trifluoromethyl, methoxy and ethoxy.

5. The compound of formula I or a pharmaceutically acceptable salt, ester, isomer, solvate, prodrug or isotopically labeled compound thereof according to claim 1, wherein
when n is an integer of 1 to 5, X—$R^1$ and Y—$R^2$ are both carbonyl.

6. The compound of formula I or a pharmaceutically acceptable salt, ester, isomer, solvate, prodrug or isotopically labeled compound thereof according to claim 1, wherein
when n is an integer from 1 to 5, each of Z is independently selected from CH and N, and each of $R^3$ is independently selected from hydrogen, deuterium, methyl, ethyl, n-propyl and iso-propyl.

7. The compound of formula I or a pharmaceutically acceptable salt, ester, isomer, solvate, prodrug or isotopically labeled compound thereof according to claim 1, wherein
n is 3, X—$R^1$ and Y—$R^2$ are both carbonyl, and each of Z—$R^3$ is independently selected from methylene (—$CH_2$—) and N-methyl secondary amino (—N($CH_3$)—), or n is 1, and Z—$R^3$ is methylene.

8. The compound of formula I or a pharmaceutically acceptable salt, ester, isomer, solvate, prodrug or isotopically labeled compound thereof according to claim 1, wherein

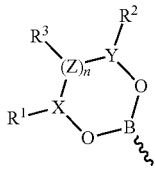

is

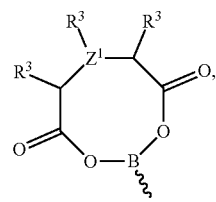

wherein $Z^1$ is O, S or N; when $Z^1$ is O or S, $R^3$ to which it is attached is absent, and each of the remaining $R^3$ is independently selected from hydrogen, deuterium, methyl and ethyl; when $Z^1$ is N, each of $R^3$ is independently selected from hydrogen, deuterium, methyl and ethyl.

9. The compound of formula I or a pharmaceutically acceptable salt, ester, isomer, solvate, prodrug or isotopically labeled compound thereof according to claim 1, wherein
when n is 0,
X and Y are directly connected, X and Y are $CR^4$ and $CR^5$ respectively,
$R^4$ and $R^5$ are each independently selected from hydrogen, deuterium, methyl and ethyl, preferably hydrogen and methyl;
$R^1$ and $R^2$ are each independently selected from hydrogen, deuterium, halogen, $C_{1-6}$ alkyl and $C_{3-8}$ cycloalkyl, preferably methyl,
Or, $R^1$ and $R^2$ are connected together to form a $C_{5-8}$ cycloalkyl which is unsubstituted or substituted with one or more, preferably 1 or 2 $R^6$, and $C_{5-8}$ cycloalkyl is

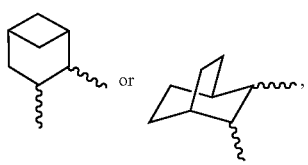

preferably

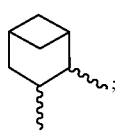

If present, each of $R^6$ is independently selected from hydrogen, deuterium, methyl and ethyl, preferably methyl;
Or, when n is 3,
$X$—$R^1$ and $Y$—$R^2$ are both carbonyl;
Each of $Z$—$R^3$ is independently selected from methylene and N-methyl secondary amino.

10. A compound or a pharmaceutically acceptable salt, ester, isomer, solvate, prodrug or isotopically labeled compound thereof, the compound is selected from the group consisting of:

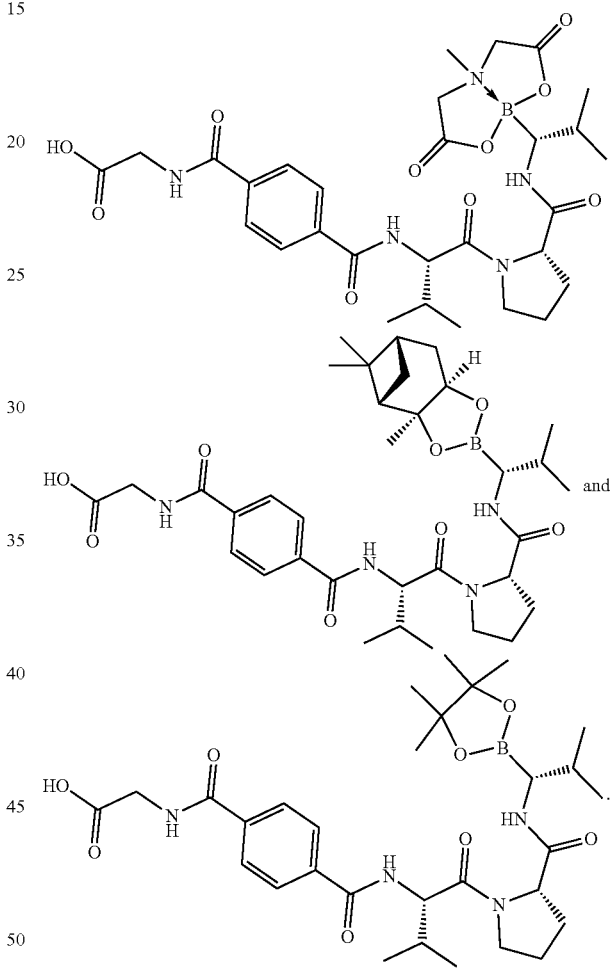

11. A pharmaceutical composition, comprising a compound according to claim 1 or a pharmaceutically acceptable salt, ester, isomer, solvate, prodrug or isotopically labeled compound thereof.

12. A pharmaceutical composition, comprising a compound according to claim 10 or a pharmaceutically acceptable salt, ester, isomer, solvate, prodrug or isotopically labeled compound thereof.

13. A method for preparing compound 13 or a pharmaceutically acceptable salt, ester, isomer, solvate, prodrug or isotopically labeled compound thereof, comprising a step of:

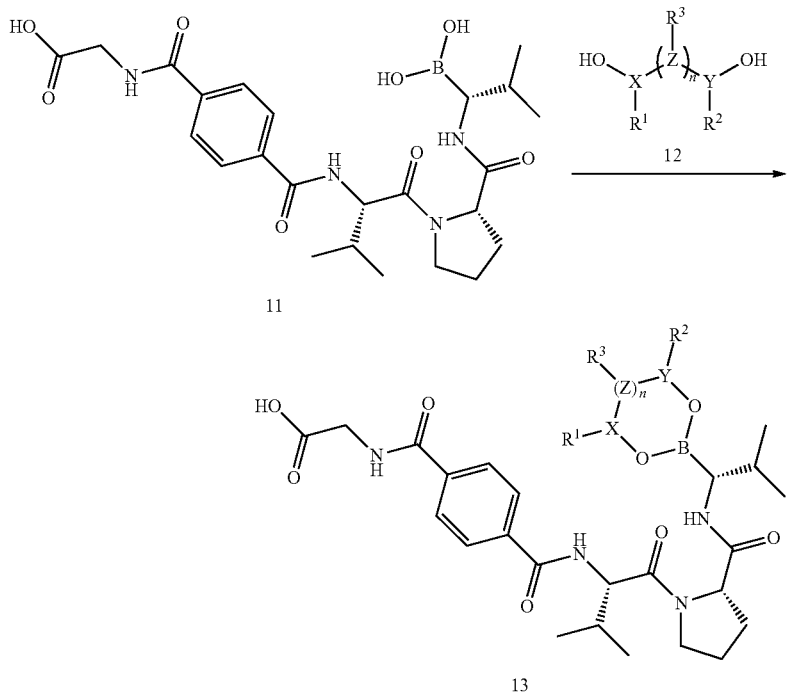

compound 11 or a pharmaceutically acceptable salt, ester, isomer, solvate, prodrug or isotopically labeled compound thereof reacts with compound 12 to obtain compound 13 or a pharmaceutically acceptable salt, ester, isomer, solvate, prodrug or isotopically labeled compound thereof, wherein:

n is an integer from 1 to 3,

X—$R^1$ and Y—$R^2$ are each independently selected from carbonyl and $CHR^7$;

if present, each of $R^7$ is independently selected from hydrogen, deuterium and $C_{1-6}$ alkyl;

each of Z is independently selected from O, S, CH and N, and when Z is O or S, $R^3$ to which it is attached is absent; and if present, each of $R^3$ is independently selected from hydrogen, deuterium and $C_{1-6}$ alkyl.

14. A method of treating a disease mediated at least in part by elastase, comprising a step of administering to a subject in need thereof a therapeutically effective amount of the compound according to claim 1 or a pharmaceutically acceptable salt, ester, isomer, solvate, prodrug or isotopically labeled compound thereof.

15. A method of treating a disease mediated at least in part by elastase according to claim 14, wherein the disease is chronic obstructive pulmonary disease.

16. A method of treating a disease mediated at least in part by elastase, comprising a step of administering to a subject in need thereof a therapeutically effective amount of the compound according to claim 10 or a pharmaceutically acceptable salt, ester, isomer, solvate, prodrug or isotopically labeled compound thereof.

17. A method of treating a disease mediated at least in part by elastase, comprising a step of administering to a subject in need thereof a therapeutically effective amount of the pharmaceutical composition according to claim 11.

18. A method of treating a disease mediated at least in part by elastase according to claim 17, wherein the disease is chronic obstructive pulmonary disease.

19. A method of treating a disease mediated at least in part by elastase, comprising a step of administering to a subject in need thereof a therapeutically effective amount of the pharmaceutical composition according to claim 12.

20. A method of treating a disease mediated at least in part by elastase according to claim 19, wherein the disease is chronic obstructive pulmonary disease.

* * * * *